US00PP08504P

United States Patent [19]

Meilland

[11] Patent Number: Plant 8,504

[45] Date of Patent: Dec. 21, 1993

[54] MINIATURE ROSE PLANT NAMED 'MEILIPO'

[75] Inventor: Alain A. Meilland, Antibes, France

[73] Assignee: The Conard-Pyle Company, West Grove, Pa.

[21] Appl. No.: 971,602

[22] Filed: Oct. 30, 1992

[51] Int. Cl.[5] ..... A01H 5/00

[52] U.S. Cl. ..... Plt./9

[58] Field of Search ..... Plt./9

[56] References Cited

U.S. PATENT DOCUMENTS

P.P. 2,140 4/1962 Meilland ..... Plt. 22

*Primary Examiner*—Howard J. Locker

*Attorney, Agent, or Firm*—Burns, Doane, Swecker & Mathis

[57] ABSTRACT

A new and distinct variety of rose plant of the miniature class is provided which abundantly forms attractive fully double Carmine Rose blossoms of stable coloration which are borne in clusters. The plant exhibits an upright growth habit, and forms very vigorous vegetation. The plant is well adapted to greenhouse forcing while grown in small containers, and is particularly well suited for use as a flowering pot plant when grown indoors or outdoors. Additionally, the plant is not particularly susceptible to diseases.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the product of the pollination of the FASHION variety (U.S. Plant Pat. No. 789) by the MEIALFI variety (also known as ZAMBRA, U.S. Plant Pat. No. 2,140). The male parent (i.e., the pollen parent) of the new variety was the MEIDANEGO variety (U.S. Plant Pat. No. 5,038). The parentage of the new variety can be summarized as follows:

(FASHION×MEIALFI)×MEIDANEGO.

The seeds resulting from the above pollination were sown and 36 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance attractive fully double blossoms which are borne in clusters and are of a stable Carmine Rose coloration,
(b) forms very vigorous vegetation,
(c) exhibits an upright growth habit,
(d) is well adapted to greenhouse forcing while growing in small containers, and
(e) is particularly suited for growing as a flowering pot plant for indoor and outdoor decoration.

The new variety well meets the needs of the horticultural industry. It is not particularly susceptible to diseases.

The new variety has been found to undergo asexual propagation in France by a number of routes, including budding, grafting, cuttage, etc. The characteristics of the new variety have been found to be strictly transmissible by such asexual propagation from one generation to another.

The new variety has been named the MEILIPO variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were observed during June while growing on their own roots outdoors at LeCannet des Maures, Var, France.

FIG. 1 — illustrates a specimen of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates specimens of two flowers during the course of opening;

FIG. 6 — illustrates a specimen of a flower in the course of opening - plan view - obverse;

FIG. 7 — illustrates a specimen of a flower in the course of opening - plan view - reverse;

FIG. 8 — illustrates a specimen of a fully open flower - plan view - obverse;

FIG. 9 — illustrates a specimen of a fully open flower - plan view - reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of leaves with three leaflets with the under surface being shown at the top and the upper surface being shown at the bottom;

FIG. 15 — illustrates specimens of leaves with five leaflets with the under surface being shown at the top and the upper surface being shown at the bottom; and FIG. 16 — illustrates specimens of leaves with seven leaflets with the under surface being shown at the top and the upper surface being shown at the bottom.

DETAILED DESCRIPTION

Figures 1, 2, 3, 4, 5, 6, 7, 8, 9, 10, 11, 12, 13, 14, 15, 16:
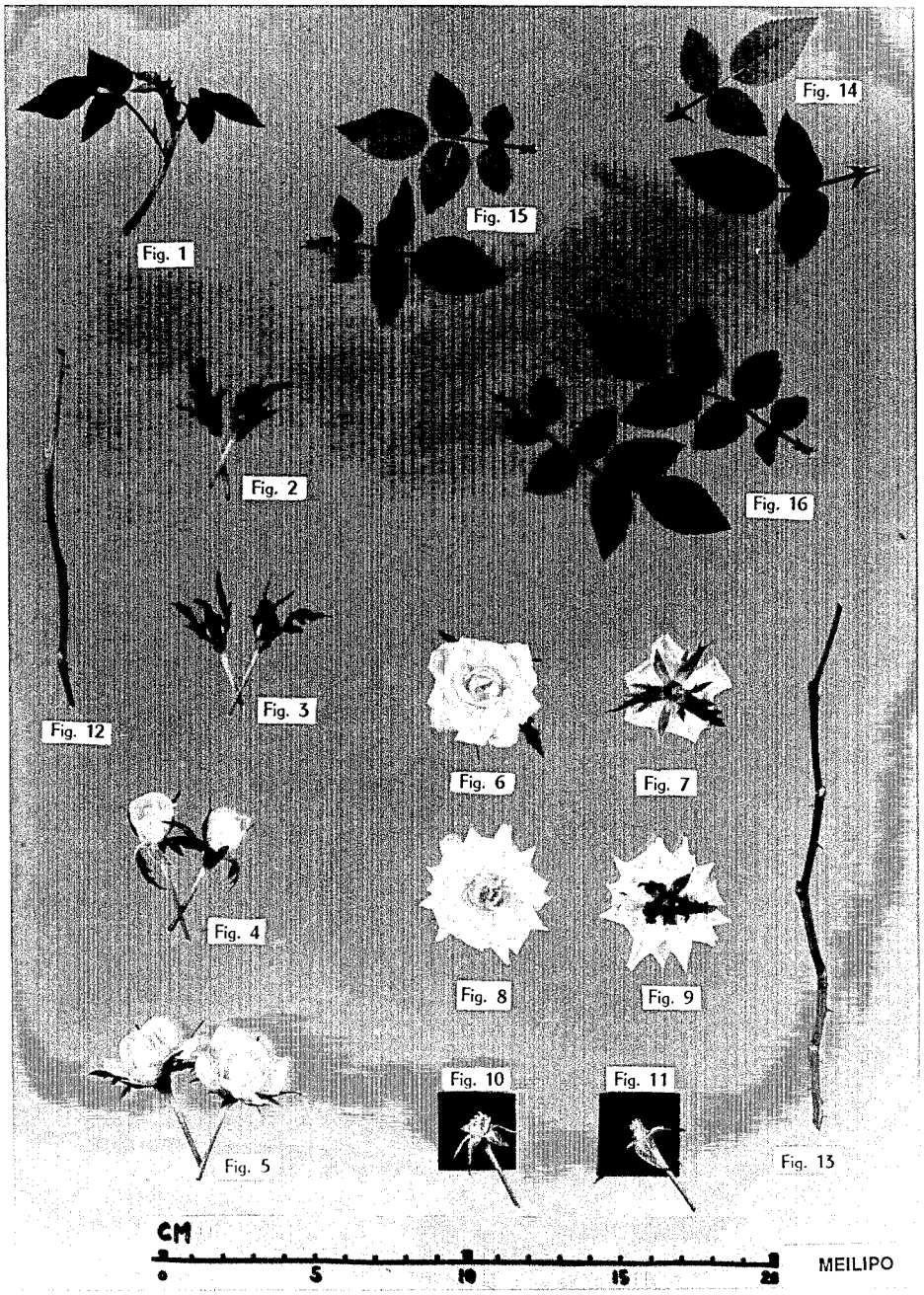

The chart used in the identification of the colors is that of The Royal Horticultural Society (R.H.S. Colour Chart). The terminology which precedes reference to the chart has been added to indicate the corresponding colors in common terms. The description is based on two year old specimens of the new variety which were observed during June while growing on their own roots outdoors at LeCannet des Maures, Var, France.

Class: Miniature.

Plant:

*Height.*—Approximately 25 to 30 cm. on average when grown outdoors on own roots in one-gallon containers.

*Habit.*—Upright.

Branches:

*Color.*—Young stems: lettuce green, Yellow-Green Group 144B. Adult wood: medium green, Yellow-Green Group 146B.

*Thorns.*—Size: small. Quantity: very few. Color: pinkish on young stems and greenish on mature wood.

Leaves:

*Petioles.*—Striped, reddish brown on young foliage and medium green on mature foliage with more or less glandular edges.

*Stipules.*—Adnate, pectinate, narrow and indented.

*Leaflets.*—Number: 3, 5 (most often), and 7. Shape: spear-shaped. Serration: single and regular. Texture: consistent. General appearance: dense, bright foliage. Color (young foliage): upper surface: light green, Green Group 143C. under surface: light green, Green Group 143C and widely suffused with reddish coloration. Color (adult foliage): upper surface: medium green, Green Group 137B. under surface: light green, Green Group 137D.

Inflorescence:

*Number of flowers.*—Approximately 2 to 5 blooms per stem.

*Peduncle.*—Smooth, light green, its length is approximately 4 to 4.5 cm. on average.

*Sepals.*—Upper surface: tomentose and greenish in coloration. under surface: medium green, and the outer sepals are slightly appendiculated.

*Buds.*—Shape: egg-shaped (i.e., ovoid). Length: approximately 1 to 1.5 cm. on average. Size: medium. Color upon opening: upper surface: Carmine Rose, Red Group 52B. Often the first petal has a greenish central vein. under surface: Carmine Rose, Red Group 52B, suffused with dark Carmine Rose, Red Group 52A.

*Flower.*—Form: as a flat cup at opening, and very double. Diameter: approximately 4 cm. on average. Color (when opening begins): upper surface: light Carmine Rose, Red Group 52C, suffused with medium Carmine Rose, Red Group 52B. Under surface: light Carmine Rose, Red Group 52C, suffused with medium Carmine Rose, Red Group 52B. Color (when blooming): upper surface: light Carmine Rose, Red Group 52C suffused with medium Carmine Rose, Red Group 52B. under surface: light Carmine Rose, Red Group 52C suffused with the medium Carmine Rose, Red Group 52B. Color (at end of blooming): upper surface: light Carmine Rose, Red Group 52C, suffused with medium Carmine Rose, Red Group 52B, turning whitish on the outer petals. under surface: light Carmine Rose, Red Group 52C, suffused with medium Carmine Rose, Red Group 52B, turning whitish on the outer petals. Fragrance: none. Petal number: approximately 68 to 70 on average. Petal texture: consistent. Petal drop: very good. Anthers: normal, yellowish in coloration. Stamen number: approximately 49 on average. Filaments: straw-like, and of irregular heights. Pistil number: approximately 70 on average. Stigmas: greenish to straw-like in coloration. Styles: fuchsia in coloration, tomentose near the base, and more or less twisted and fused. Receptacle: light green, and in longitudinal section is wide and in the shape of a pitcher at the dehiscence of the anthers.

Development:

*Vegetation.*—Very vigorous.

*Blooming.*—Very abundant even under low light conditions.

*Resistance to diseases.*—Fair.

I claim:

1. A new and distinct variety of miniature rose plant characterized by the following combination of characteristics:

(a) forms in abundance attractive fully double blossoms which are borne in clusters and are of a stable Carmine Rose coloration,
(b) forms very vigorous vegetation,
(c) exhibits an upright growth habit,
(d) is well adapted to greenhouse forcing while growing in small containers, and
(e) is particularly suited for growing as a flowering pot plant for indoor and outdoor decoration;

substantially as herein shown and described.

* * * * *

CM
0
5
10
15
20
MEILIPO